US006753189B1

(12) United States Patent
Narahara et al.

(10) Patent No.: US 6,753,189 B1
(45) Date of Patent: Jun. 22, 2004

(54) DETECTION APPARATUS AND METHOD FOR THE SAME

(75) Inventors: Kenji Narahara, Tosu (JP); Toshiyuki Uehara, Tosu (JP)

(73) Assignee: Mizuho Medy Co., Ltd., Saga-Ken (JP)

( * ) Notice: Subject to any disclaimer, the term of this patent is extended or adjusted under 35 U.S.C. 154(b) by 0 days.

(21) Appl. No.: 09/325,214

(22) Filed: Jun. 3, 1999

(30) Foreign Application Priority Data

Jun. 4, 1998 (JP) ............................................ 10-156165
Jun. 4, 1998 (JP) ............................................ 10-156169

(51) Int. Cl.$^7$ ............................................ G01N 33/543
(52) U.S. Cl. ........................ 436/514; 435/7.1; 435/7.94; 435/287.7; 435/287.8; 436/518; 436/523; 436/538; 436/541; 436/810; 436/823; 436/824; 422/56; 422/60; 422/101
(58) Field of Search .............................. 436/514, 518, 436/523, 538, 541, 810, 823, 824; 435/7.1, 7.94, 287.7, 287.8; 422/56, 60, 101

(56) References Cited

U.S. PATENT DOCUMENTS

| | | | |
|---|---|---|---|
| 3,992,158 A | * | 11/1976 | Przybylowicz et al. |
| 4,469,787 A | * | 9/1984 | Woods et al. |
| 4,772,550 A | * | 9/1988 | Greenquist |
| 4,806,311 A | * | 2/1989 | Greenquist |
| 4,853,335 A | | 8/1989 | Olsen et al. |
| 4,859,612 A | * | 8/1989 | Cole et al. |
| 5,141,850 A | * | 8/1992 | Cole et al. |
| 5,202,267 A | * | 4/1993 | Ditlow et al. |
| 5,236,826 A | * | 8/1993 | Marshall |
| 5,602,040 A | | 2/1997 | May et al. |
| 5,622,871 A | | 4/1997 | May et al. |
| 5,656,503 A | | 8/1997 | May et al. |
| 6,228,660 B1 | | 5/2001 | May et al. |
| 6,352,862 B1 | | 3/2002 | Davis et al. |

FOREIGN PATENT DOCUMENTS

| | | |
|---|---|---|
| EP | 0505636 | 9/1992 |
| JP | 05052849 | 3/1993 |
| JP | 09274039 | 10/1997 |
| JP | 10090267 | 4/1998 |
| WO | 9726083 | 7/1997 |
| WO | 9822800 | 5/1998 |
| WO | 9838513 | 9/1998 |

OTHER PUBLICATIONS

Bangs, L.B., New developments in particle–based tests and immunoassays. JiFCC. vol. 2, No. 4. pp. 188, 190–193. 1990.*

* cited by examiner

Primary Examiner—Bao-Thuy L. Nguyen
(74) Attorney, Agent, or Firm—Darby & Darby

(57) ABSTRACT

A catcher, having an immunological epitope, is fixed to a detection zone of a spreading layer. A marker, capable of easy detection, has an inmmunological epitope. The marker and bispecific antibodies are soluble so that they can move on the spreading layer. The bispecific antibodies include a first bispecific antibody, having specificity for the detectable material in the fluid sample and the marker, and a second bispecific antibody, having specificity for the detectable material in the fluid sample and the catcher. Pore sizes and particle diameters are set so that the reaction product in which the marking elements and the particles are bonded are caught at a catching section. The concentration of the marking elements and the particles are increased to improve detection sensitivity. The result is an inexpensive and simple detection apparatus being highly-sensitive for the immunological detection of a detectable material, without wasting valuable antibodies.

6 Claims, 4 Drawing Sheets

DETECTION APPARATUS AND METHOD FOR THE SAME

BACKGROUND OF THE INVENTION

The present invention relates to a detection apparatus for detecting the presence of a detectable material in a sample. More specifically, the present invention relates to a detection apparatus for detecting the presence of a biological component in urine, blood, or the like. Additionally, the present invention relates to a method for the detection of a biological component in urine, blood, or the like.

Among conventional detection methods for detecting a biological component detectable material, there is an immunological detection method, which uses antibodies and antigens. This method, which provides high sensitivity and good specificity and ease of use, is used widely in the field of clinical testing. Various technologies have been recently proposed to perform testing using the immunological detection method without requiring any special techniques or training.

Of these, a group of measuring methods known as immunological chromatography has been proposed (Japanese laid-open patent publication number 9-178748) and is already being marketed to the general population. This method provides quick, easy, and accurate results.

In immunological chromatography, a marked reagent (staining indicator) using colored latex, colloidal gold, or the like, is fixed to a spreading layer. An unmarked reagent is fixed to a detection zone on the spreading layer. When the detectable material is present in the fluid sample, immunoreaction compounds are produced. The staining marker from this reaction is caught so that it can be visually observed. With the immunological chromatography method, the fluid sample can be simply applied to an application position. After a fixed period of time, the degree of coloration from the staining marker is observed at the detection zone.

With this method, the antigens or antibodies which have affinity for the detectable material must be prepared along with enzymes, fluorescent materials, luminescent materials, colored latex, colloidal gold, or the like, which serve as markers, that are chemically or physically bonded with marker antigens or marker antibodies depending on the application. However, the marking reaction involves a major problem. For example, to bond an enzyme to an antigen or antibody protein, a chemical procedure such as periodic acid oxidation can be performed (Enzyme Immunoassay, Igaku-Shoin, Tokyo, 1982). In such cases, irreversible deactivation of the antigen, antibody, or the enzyme takes place. Additionally, polymerization leading to reduction of activation or non-specific reaction can take place. As a result, the practical marker yield becomes very low.

Similarly, when physical (hydrophobic bonding) methods are used to bond colored latex to antigen or antibody proteins, the bonding to the colored latex takes place randomly so that the active sites of the antigen or antibodies are lost. This provides inadequate reactions so that excess antigens or antibodies must be used. Also, since absorption does not proceed 100%, significant antigens or antibodies are wasted.

To overcome these problems, a method that uses bivalent reagents, as a crosslinking agent, has been developed (Enzyme Immunoassay, Igaku-Shoin, Tokyo, 1982). However, the operations involved are complex and require a high degree of skill. Furthermore, since the reaction itself is highly sensitive, slight changes in reaction conditions can greatly affect the properties of the marker. Thus, the bivalent reagent method of preparing markers is considered not very reproducible.

When using the conventional high-specificity marking method, the loss of activation of the markers or the antigens/antibodies or the like is unavoidable, and 100% marking cannot be achieved since the marking operation is itself a chemical reaction.

OBJECTS AND SUMMARY OF THE INVENTION

It is an object of the present invention to provide a detection method for minimizing reduced activation and antibody loss from the marking operation while providing measurement sensitivity that is at least equal to that of the conventional technology.

It is a further object of the present invention is to provide a detection apparatus that gives highly sensitive and inexpensive immunological detection without wasting valuable antibodies.

It is another object of the present invention to provide a detection method that gives highly sensitivity and inexpensive immunological detection without wasting valuable antibodies.

It is still a further object of the present invention to provide a high-sensitivity detection apparatus and method for detecting a detectable material that does not involve restrictions of reagent amounts.

Briefly stated, the present invention provides a catcher, having an immunological epitope, fixed to a detection zone of a spreading layer. A marker, capable of easy detection, has an immunological epitope. The marker and bispecific antibodies are soluble so that they can move on the spreading layer. The bispecific antibodies include a first bispecific antibody, having specificity for the detectable material in the fluid sample and the marker, and a second bispecific antibody, having specificity for the detectable material in the fluid sample and the catcher. Pore sizes and particle diameters are set so that the reaction product in which the marking elements and the particles are bonded are caught at a catching section. The concentration of the marking elements and the particles are increased to improve detection sensitivity. The result is an inexpensive and simple detection apparatus being highly-sensitive for the immunological detection of a detectable material, without wasting valuable antibodies.

In the conventional detection apparatus, as described above, the unmarked reagent is fixed to the detection zone on the spreading layer. With this structure, the amount of reagent is restricted by its ability to bond with protein. Thus, it is difficult to use more than a fixed amount. Also, in order to detect the detectable material, the detectable material must be biologically bonded to both the reagent component and the marking component. The restriction on the amount of reagent prevents the sensitivity from going beyond a certain point.

Furthermore, the reagent is fixed to the spreading layer. Therefore, out of the time that the detectable material is chromatographically moving along the spreading layer, the reaction can only take place during the very short interval of time when the detectable material contacts the reagent. This reduces the reaction and results in low reactivity in the conventional detection device. With regard to this problem, a technology has been proposed to use magnetism (Japanese laid-open patent publication number 5-52849), but this requires the use of materials having magnetism and therefore cannot be applied to a wide range of materials.

According to an embodiment of the present invention, there is provided a detection apparatus for detecting the presence of a detectable material in a sample comprising: a spreading layer on which the sample is applied; a catcher fixed to the spreading layer at a detection zone away from a position at which the sample is applied; the catcher including an immunological epitope; bispecific antibodies supported in the spreading layer in a dry state, such that movement of the bispecific antibodies is possible when the bispecific antibodies are in a soluble state; a marker supported in the spreading layer in a dry state, such that movement of the marker is possible when the marker is in a soluble state; the marker including an immunological epitope being capable of detection; the double-specific antibody including a first double-specific antibody and a second double-specific antibody; the first double-specific antibody being specific to the detectable material in the sample as well as the marker; and the second double-specific antibody being specific to the detectable material in the sample as well as the catcher.

According to another embodiment of the present invention, there is provided a detection method for detecting the presence of a detectable material in a sample comprising: applying the sample to one end of a spreading layer such that the sample chromatographically moves in a direction toward the other end of the spreading layer; solubilizing a first bispecific antibody, a second bispecific antibody, and a marker, thereby permitting movement of the first bispecific antibody, the second bispecific antibody, and the marker along the spreading layer; bonding the detectable material with the first bispecific antibody and the second bispecific antibody such that the detectable material is interposed therebetween; bonding the first bispecific antibody with the marker; bonding the second bispecific antibody with a catcher fixed to the spreading layer at a detection zone located a prescribed distance from a point where the sample was applied to the spreading layer; and analyzing presence of the marker at the detection zone, whereby the presence of the marker corresponds with presence of the detectable material.

According to a further embodiment of the present invention, there is provided a detection apparatus for detecting the presence of a detectable material in a sample comprising: a fluid application section contacting the sample; a reaction reagent section, having particles and marking elements movably contained therein, connected to the fluid application section such that the sample moves from the fluid application section to the reaction reagent section; a porous carrier connected to the reaction reagent section such that the sample moves from the reaction reagent section to the porous carrier; a reaction product formed from biologically bonding the detectable material with both the marking elements and the particles when the detectable material is present in the sample; and a catching section in the porous carrier made from a material having a pore size smaller than a size of the reaction product, such that chromatographic movement of the marking elements not bonded to the particles is permitted through said catching section and chromatographic movement of the reaction product is restricted.

According to still another embodiment of the present invention, there is provided a detection method for detecting the presence of a detectable material in a sample comprising: contacting the sample with a fluid application section; chromatographically moving the sample through the fluid application section, a reaction reagent section, and a porous carrier; reacting the sample with particles and marking elements contained in the reaction reagent section to form a reaction product, such that the detectable material bonds with both the marking elements and the particles when the detectable material is present in the sample; passing the sample, including any reaction product present, through a catching section having a pore size smaller than a size of the reaction product and larger than a pore size of the marking elements; and analyzing presence of the marking elements at the catching section, whereby presence of the marking elements corresponds to presence of the detectable material.

A detection apparatus according to the present invention includes a spreading layer onto which a fluid sample is applied. A detection zone is disposed on the spreading layer at a position away from the position at which the fluid sample is applied. A catcher containing an immunological epitope is fixed to the detection zone. A detectable marker contains an immunological epitope. The marker and bispecific antibodies are supported in a dry state in the spreading layer so that when soluble they can move. The bispecific antibodies contain a first bispecific antibody, which has specificity for the marker and the detectable material in the fluid sample, and a second bispecific antibody, which has specificity for the catcher and the detectable material in the fluid sample.

A detection apparatus according to the present invention includes a fluid application section placed in contact with the sample fluid, a reaction reagent section connected to the fluid application section, and a porous carrier connected to the reaction reagent section. The reaction reagent section contains particles, which do not affect detection, and marking elements which, through biochemical reactions, bond with the particles through the detectable material. The particles and the marking elements are able to move through the porous carrier. A catching section, disposed at the detection zone, prevents chromatographical movement of the reaction product produced from the bonding of the particles and the marking elements with the detectable material. The catching section also allows chromatographic movement of marking elements not bonded with particles. The pore size of the catching section is smaller than the particle diameter of the reaction product and is larger than the particle diameter of the marking elements not bonded with particles.

The detection apparatus according to the present invention includes a spreading layer on which a fluid sample is applied. A catcher is fixed to the spreading layer at a detection zone away from a position at which the fluid sample is applied. The catcher includes an immunological epitope. Bispecific antibodies and a marker are supported in the spreading layer in a dry state so that movement is possible when in a soluble state. The marker includes an immunological epitope and is capable of being detected. The bispecific antibodies include a first bispecific antibody and a second bispecific antibody. The first bispecific antibody is specific to a detectable material in the fluid sample as well as the marker. The second bispecific antibody is specific to the detectable material in the fluid sample as well as the catcher.

With this structure, detection is performed without the use of marker antibodies. Thus, there is no antibody loss for marking operations. Since no special equipment is needed, costs are reduced. The activation of the antibodies is not reduced. Since bispecific antibodies are used, the antigen-antibody reaction provides improved reactivity and sensitivity.

In the detection method of the present invention, a fluid sample is applied to a spreading layer from the detection apparatus described above. The bispecific antibodies and the marker are put in a soluble state (which includes states where fine particles are dispersed), where they are allowed to move through the spreading layer. The first bispecific antibody and the second bispecific antibody bond so as to have the detectable material interposed. The first bispecific antibody is bonded to the marker. The second bispecific antibody is bonded to the catcher. At the detection zone, detection results are produced in an amount corresponding to the amount of the detection material in the fluid sample.

With this structure, detection is completed simply by applying the fluid sample, waiting for a fixed period of time, and viewing the detection results at the detection zone.

The detection apparatus according to a feature of the present invention includes a fluid application section contacting a fluid sample. A reaction reagent section connects to the fluid application section. A porous carrier connects to the reaction reagent section. The reaction reagent section includes particles not affecting detection and marking elements. The marking elements bond, through a biochemical reaction, to the particles and the detectable material when the detectable material is present. The particles and the marking elements are movably contained in the porous carrier. A reaction product, produced from bonding between the particles and the marking elements to the detectable material, prevents chromatographic movement of the reaction product. A catching section is disposed at a detection zone to allow chromatographic movement of the marking elements not bonded to the particles. The pore size of the catching section is smaller than the particle diameter of the reaction product and is larger than the particle diameter of the marking element not bonded to the particles.

With this structure, the unmarked reagent is not solidified in the porous carrier and is simply contained in the reaction reagent section. Thus, the amount of unmarked reagent is not restricted by the need to perform solidification. This allows a greater amount of unmarked reagent to be used compared to the conventional detection apparatus, providing improved detection sensitivity. Furthermore, since the unmarked reagent is not physically bound to the porous carrier, the unmarked reagent moves freely through the porous carrier and the free motion (collisions) between components efficiently promotes and speeds up the reaction compared to the conventional technology. This provides improved detection.

Also, if the detectable material is present, the marker bonds with the particles to form a reaction product, which is then caught at the catching section. Thus, there is no hindrance in obtaining the detection results.

Furthermore, the relationship between the pore size and the particle diameter allows the reaction product produced by the bonding between the marking element and the particles to stop and be caught at the catching section.

In the detection apparatus according to another feature of the present invention, the pore size of the catching section is smaller than the particle diameter of the particle.

With this structure, unbonded particles are also stopped at the catching section. This relationship between the diameters can be used when the detectable material has only one immunological reaction site of the same type. In this case, the reaction product and a single particle have roughly the same size, allowing the reaction product to stop at the catching section.

In the detection apparatus according to a further feature of the present invention, the pore size of the catching section is larger than the particle diameter of the particle.

With this structure, unbonded particles pass through the catching section. The relationship between the diameters is suitable for when the detectable material has multiple immunological reaction sites of the same type. In such cases, the detectable material bonds with multiple particles so that the reaction product develops into an aggregate that is much larger than a single particle. Unless the particles are made smaller, the aggregate will become so large that the reaction products can get caught in the middle of the porous carrier without reaching the catching section. Therefore, the particle diameter should be made small to allow the reaction product to chromatographically move to the catching section.

The above, and other objects, features and advantages of the present invention will become apparent from the following description read in conjunction with the accompanying drawings, in which like reference numerals designate the same elements.

DETAILED DESCRIPTION OF THE PREFERRED EMBODIMENTS

First Embodiment

Figure 1:
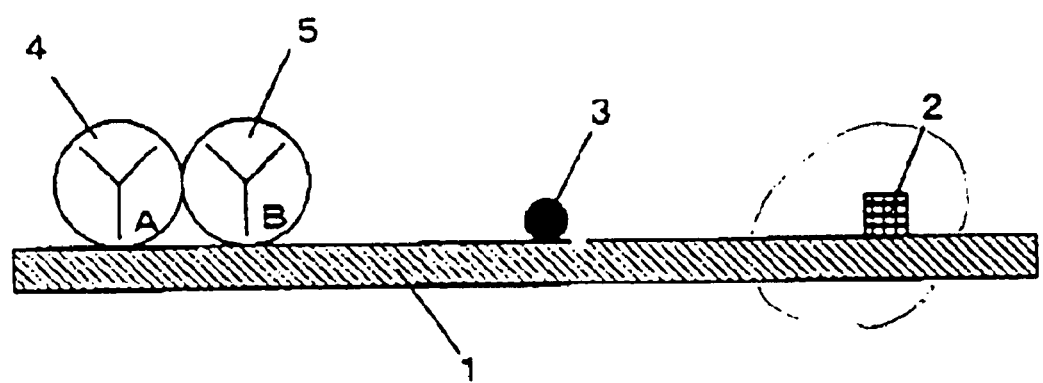
FIG. 1 is a schematic drawing illustrating the principles involved in a detection apparatus according to a first embodiment of the present invention.
Figure 2:
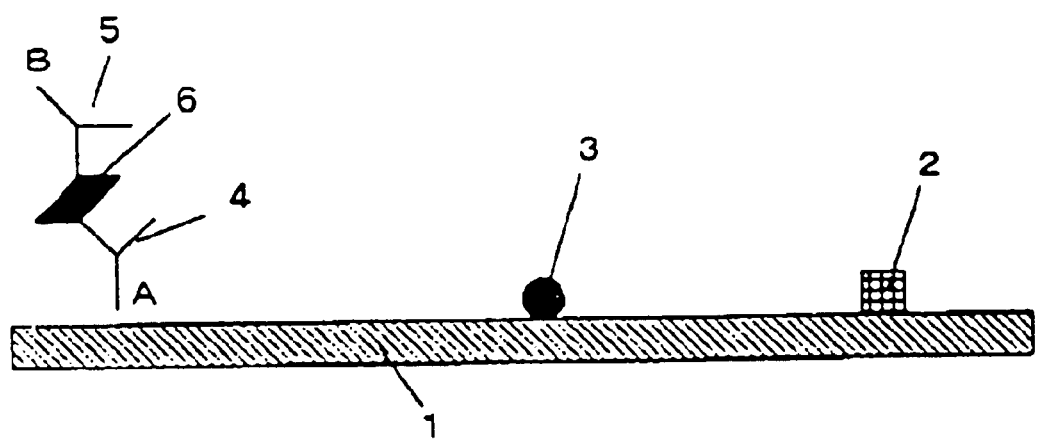
FIG. 2 is a drawing describing the detection process according to the first embodiment of the present invention.
Figure 3:
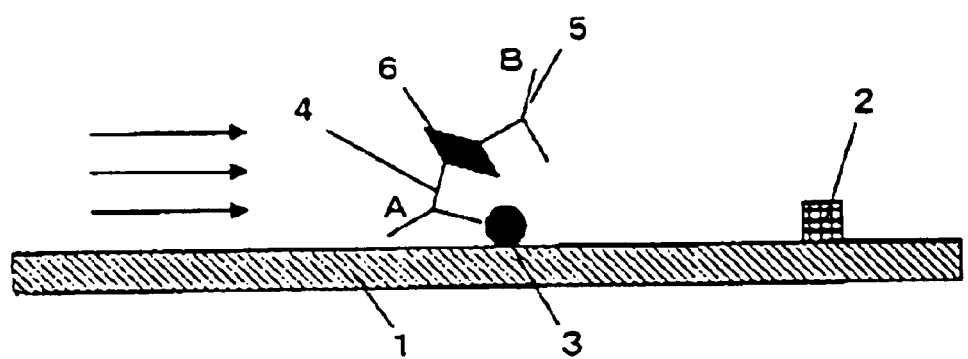
FIG. 3 is a drawing describing the detection process according to the first embodiment of the present invention.

Referring to FIG. 1, a spreading layer 1 of a detection apparatus is stored in a dry state. Spreading layer1, serving as a reaction support, is formed from a porous material or a single-pore material. A fluid sample is applied to an application position (at the left hand side of the figure). When the fluid sample is applied to the application position, capillary action causes the fluid sample to move from the left to the right.

Each of the remaining components are stored in a dry state on spreading layer1. A catcher 2 is fixed to the end opposite the application position (the detection zone). Catcher 2 contains an immunological epitope (antigenic determinant). As described later, a detectable material is bonded with a marker via a bispecific antibody. The movement of the bonded detectable material is stopped at the detection zone by catcher 2, which acts against the flow of the fluid sample.

A marker 3 is disposed between the application position and the detection zone. Marker 3, containing an immunological epitope, allows detection through electrical, chemical, or visual means, or the like. Marker 3 can be either a soluble material or an insoluble coloring particle.

Marker 3 can itself contain epitope. Alternatively, it is also possible to chemically or physically combine a marker that does not originally contain epitope with a material that contains epitope. In this embodiment, a colored marker that can be visually inspected is used for marker 3.

Two bispecific antibodies 4 and 5 are supported near the application position. Of these, first bispecific antibody 4 has specificity with relation to a detectable material 6 in the fluid sample as well as with marker 3. Second bispecific antibody 5 has specificity with relation to detectable material 6 in the fluid sample and with catcher 2.

The bispecific antibodies described herein refer to antibodies that can bond simultaneously with two different types of epitopes. The antibodies described herein refer to uniform protein molecule antibodies and not to polyclonal antibodies in which antibodies are mixed.

The bispecific antibody herein is a synthetic product that cannot generally be obtained from animal species. Three methods can be used to synthesize these bispecific antibodies. The first method is a cellular engineering method (Behrsing, O. et al; J. Immunol. Methods, 156 (1), 69–77, 1992. Takahashi, M. et al; Clin. Chem. 34 (9),1693–96, 1988, Suresh, M. R. et al; Methods Enzymol. 121 (Immunochem. Tech. Pt. I. 210–28, 1986)). In the cellular engineering method, a hybridoma A producing a monoclonal antibody A is fused with a hybridoma B producing a monoclonal antibody B to form a new fused cell (quadroma), thus producing a molecule that is a hybrid of monoclonal antibody A and monoclonal antibody B.

The second method is a protein chemistry method (Brennan, M. et al; Science, 229,81–3,1985, Parham, P.; Hum. Immunol., 12,213–21, 1985, Glennie, M. J. et al; J. Immunol. 139 (7), 2367–75,1987). In the protein chemistry method, a disulfide bond between monoclonal antibody A and monoclonal antibody B is reduced to form a half molecule. The half molecule formed from monoclonal antibody A and monoclonal antibody B is reassociated to create a molecule that is a hybrid of the monoclonal antibodies A and B.

The third method is a genetic engineering method (Songsiviliai, S. et al; Biochem. Biophysics. Res. Commun., 164 (1), 271–6, 1989). In the genetic engineering method, a gene is prepared so that the antigen bonding positions of monoclonal antibody A and monoclonal antibody B are expressed as a single polypeptide molecule. Of these methods, the desired bispecific antibody can be produced relatively easily using the first and the second methods.

Referring to FIGS. 1 through 4, the different components are drawn on the surface of spreading layer1. This is done to facilitate the rendering, however, these different components actually exist inside spreading layer1.

A fluid sample is applied to the application position, which is at the left end in FIG. 1. This causes bispecific antibodies 4 and 5, which are dried and solid, to dissolve, allowing them to move within spreading layer1.

If detectable material 6 is present in the fluid sample, detectable material 6 bonds with the first and the second bispecific antibodies 4 and 5 in such a manner that detectable material 6 is interposed between the first and the second bispecific antibodies 4 and 5.

Capillary action within spreading layer1 causes the fluid sample to move gradually to the right, causing first bispecific antibody 4, to also move rightward inside spreading layer 1. An antigen-antibody reaction takes place between first bispecific antibody 4 and marker 3, bonding together first bispecific antibody 4 with marker 3.

When this bonded product reaches the detection zone, second bispecific antibody 5 encounters catcher 2, resulting in an antigen-antibody reaction. This reaction causes second bispecific antibody 5 to bond with catcher 2.

As a result, second bispecific antibody 5 becomes bonded to marker 3 via detectable material 6 and first bispecific antibody 4. Thus, marker 3 is also fixed to the detection zone so that it stays at the detection zone even when the fluid sample flows away.

If detectable material 6 is absent, first bispecific antibody 4, which bonds to marker 3, does not connect with catcher 2. Thus, marker 3 moves past the detection zone (rightward). Marker 3 does not remain at the detection zone when detectable material 6 is absent.

Figure 4:
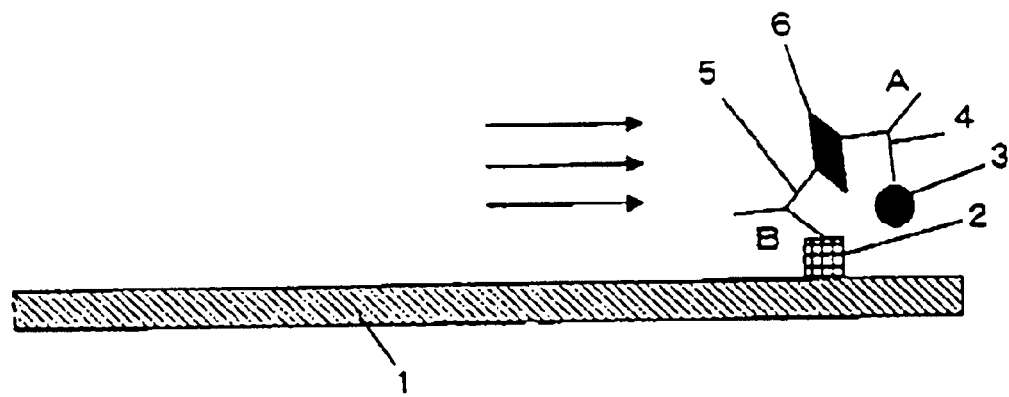
FIG. 4 is a drawing describing the detection process according to the first embodiment of the present invention.

After applying the fluid sample and waiting a fixed period of time for the state shown in FIG. 4, the amount of marker 3 present at the detection zone will correspond to the amount of detectable material 6. Thus, the detection results are easily obtained by visually inspecting the detection zone.

As a result, a positive or negative evaluation is made by looking at the coloring at the detection zone caused by marker 3.

Second Embodiment

Figures 5A, 5B:
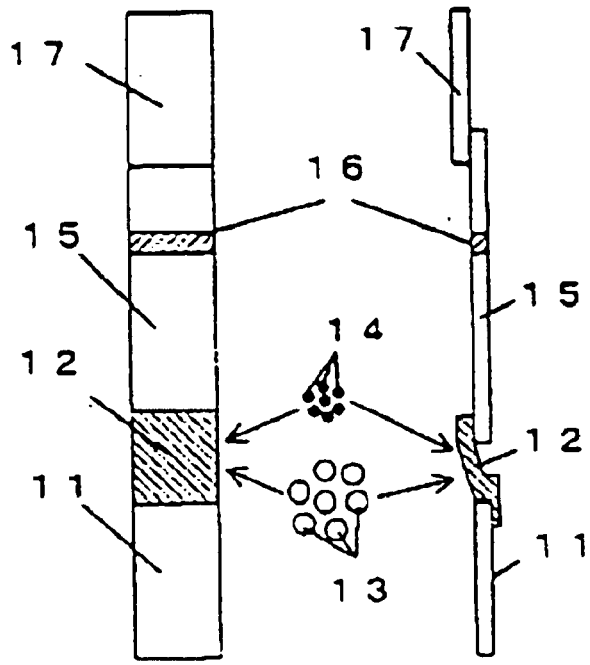
FIG. 5(a) is a front-view drawing of a detection apparatus according to a second embodiment of the present invention.
FIG. 5(b) is a side-view drawing the detection apparatus of FIG. 5 (a).

Referring to FIGS. 5(a) and 5(b), in the second embodiment of the present invention, the particle diameter of particles 13 is greater than the pore size of a catching section 16. This embodiment is useful for cases where a detectable material T (see FIG. 6(c)) has just one immunological reaction site of the same type. Examples of detectable material T include hCG (human chorionic gonadotropin), LH (luteinizing hormone), FSH (follicle stimulating hormone), TSH (thyroid stimulating hormone), insulin, and CEA (carcinoembryonic antigen).

Figure 6A:
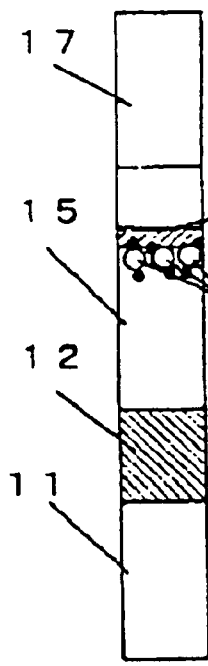
FIG. 6(a) is a front-view drawing of a detection apparatus according to a second embodiment of the present invention (positive).
Figure 6B:
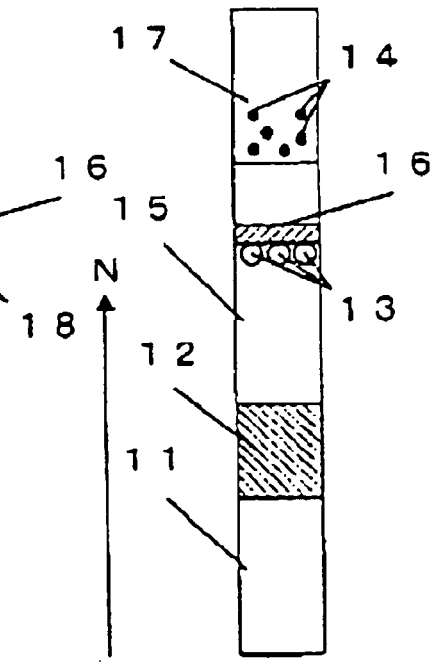
FIG. 6(b) is a front-view drawing of the detection apparatus according to a second embodiment of the present invention (negative).
Figure 6C:
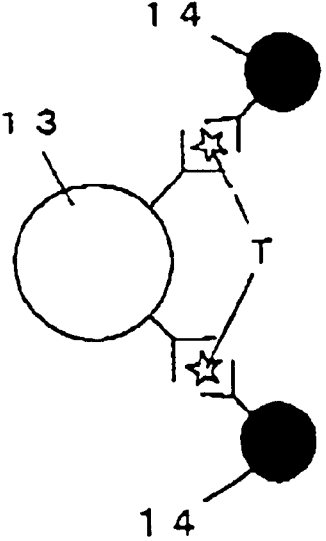
FIG. 6(c) is a close-up view of the detection apparatus of FIG. 6 (a).

Referring to FIGS. 6(a), 6(b), and 6(c), a fluid application section 11, preferably formed from a filter paper, contacts the fluid sample by dripping the fluid sample onto the filter paper or by immersing the filter paper in the fluid sample. A reaction reagent section 12, continuous with fluid application section 11, contains particles 13 and marking elements 14.

Particles 13 do not affect the evaluation. If the evaluation is performed visually, particles 13 are white or transparent. When detectable material T is present, a biochemical (e.g., immunological) reaction takes place between marking elements 14 and particles 13, producing a reaction product 18.

A porous carrier 15 serves as a reaction support body. The pore size of porous carrier 15 is set to be larger than the particle diameters of particles 13 and the size of reaction products 18. Marking elements 14, particles 13, and reaction product 18 are able to freely move chromatically through porous carrier 15.

A catching section 16 is disposed at an intermediate position (detection zone) in porous carrier 15. The pore size of catching section 16 is set to be smaller than the particle diameter of particles 13 and the size of reaction product 18, but larger than the particle diameter of marking element 14. Catching section 16 is sandwiched between and linked in series with two porous carriers 15.

If necessary, a fluid absorption section 17, formed from filter paper or the like, is connected to porous carrier 15 to allow the fluid sample to move chromatically. In this second embodiment, the spreading layer is formed from fluid collection section 13, porous carrier 15, and fluid absorption section 17.

When fluid application section 11 contacts the fluid sample, the fluid sample begins moving in the direction indicated by an arrow N. Then, when the fluid sample reaches reaction reagent 12, particles 13 and marking elements 14 in reaction reagent section 12 begin moving together with the fluid sample. Since particles 13 are not fixed to porous carrier 15 they can move freely.

If the detectable material T is present in the fluid sample, reaction product 18 is produced in porous carrier 15, as shown in FIG. 6(c). The bonding between particle 13 and detectable material T as well as the bonding between detectable material T and marking elements 14 result in a bond between marking elements 14 and particle 13 via detectable material T. Reaction product 18 from the second embodiment has a size that is roughly similar to that of particles 13. If the detectable material T is not present, reaction product 18, as shown in FIG. 6(c), would not be formed. Instead, marking elements 14 and particles 13 would move separately as shown in FIG. 6(b).

When catching section 16 is reached, particles 13 and reaction product 18 are caught by catching section 16 and cannot proceed further. Marking element 14, however, is able to pass through catching section 16 to reach fluid absorption section 17.

If the detectable material T is present and the results are positive, reaction products 18 are kept at catching section 16. Marking elements 14, being a part of reaction products 18, stay at catching section 16 as well. Conversely, if no detectable material T is present and the results are negative, only particles 13 are kept at catching section 16. Marking elements 14 pass through catching section 16 without stopping at catching section 16.

As a result, a visual inspection or sensing can be performed on catching section 16 to determine if the results are positive or negative.

In the description above, catching section 16 has a smaller pore size and is linked in series with porous carrier 15. However, the present invention is not restricted to this structure. For example, it is also possible to reduce the effective pore size of porous carrier 15 itself to use it as a substitute for catching section 16. This can be achieved by applying heat treatment or chemical treatment on porous carrier 15, or by applying chemical or physical processing in order to embed particles, such as white latex, in porous carrier 15.

In the second embodiment, as described above, detection is performed without having to fix marking elements 14 onto porous carrier 15. As a result, the conventional technology's restrictions on the amount of particles and marking elements that can be used are eliminated while the reaction volume itself can be greatly increased, thus improving the sensitivity of detection.

Also, since the concentrations for particles 13 and marking elements 14 can be adjusted freely, production control is made easier. In the production process used for the conventional detection apparatus, it is necessary to fix the making elements and perform special steps in order to improve the reliability of the flow through the porous carrier. The present invention reduces the burden of these steps.

EXAMPLE 1

In example 1 the detectable material is the pregnancy marker hCG. Example 1 is performed according to the second embodiment described above.

(1) Elements

Anti-beta hCG antibody was bonded to 1 micron white latex, serving as particle 13. Anti-hCG antibody was bonded to 0.3 micron colored latex or 0.02 micron colloidal gold. Bonding was performed using standard methods.

The reaction reagent was formed in the following manner. For the particles, 4.8 microliters were used per test at 0.1% concentration. When colored latex was used for the marking element, 3.6 microliters were used per test at 0.3% concentration. When colloidal gold was used for the marking element, 4.8 microliters were used per test at a concentration that provides absorbency of 5.0 for light at 520 nm. The reaction reagents were mixed and applied to an intermediate portion of a fiberglass pad, which served as the porous carrier. For the fluid application section, filter paper was connected to the fiberglass pad. A nitrocellulose membrane (trade name SCHF from Millipore Corp.) was used as the catching section. These were combined to form the detection apparatus.

(2) Tests and Results

Eighty microliters, each of a positive sample containing hCG and a negative sample not containing hCG, were absorbed into the fluid application sections. After five minutes, the coloring at the catching sections was observed. For the sample containing hCG, coloring formed by the marking element appeared at the catching section in a range of 50 mIU/ml–1,000,000 mIU/ml. For the sample not containing hCG, no coloring was observed and a negative evaluation was made.

Third Embodiment

Figure 7:
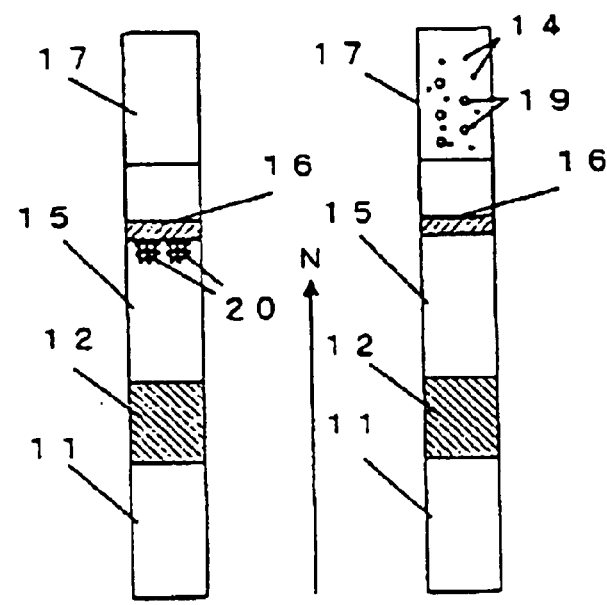
FIG. 7(a) is a front-view drawing of a detection apparatus according to a third embodiment of the present invention (positive).
FIG. 7(b) is a front-view drawing of the detection apparatus according to a third embodiment of the present invention (negative).
FIG. 7(c) is a close-up view of the detection apparatus of FIG. 7 (a).
Figure 7:
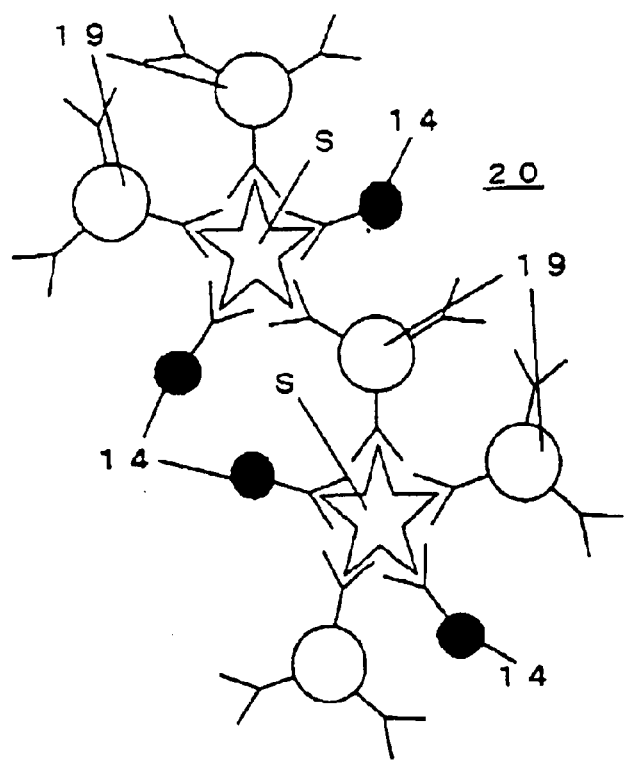

Referring to FIGS. 7(a), 7(b), and 7(c), in the third embodiment of the present invention, the particle diameter of a particle 19 is less than the pore size of catching section 16. In this embodiment, a detectable material S has multiple immunological reaction sites of the same type. Examples of the detectable material S include HBsAg (hepatitis B surface antigen), CRP (C-reactive protein), hemoglobin, and various antibodies (antibody detect).

The third embodiment differs from the second embodiment in the relationship between particle diameter and pore size as well as the properties of detectable material S. When detectable material S has multiple immunological reaction sites of the same type, a single detection material S can bond with multiple particles 19. In addition, particles 19 can bond with other detectable materials S. When this type of chained bonding takes place, a reaction product 20 becomes an aggregate of multiple particles 13. The size of this aggregate is much greater than the size of single particle 13. If the size of particle 13 increases, the size of reaction product 20 will increase roughly proportionally. This can result in reaction product 20 stopping in the middle of porous carrier 15 so that reaction product 20 cannot move chromatographically as shown by arrow N. This makes it impossible to determine a positive or negative evaluation in catching section 16.

Therefore, the relation between particle diameter and pore size is such that the particle diameter of particles 19 is less than the pore size of catching section 16. In this configuration, reaction products 20, which have grown large, will be stopped at catching section 16. When no reaction products 20 are formed, however, particles 19 and marking elements 14 will pass through catching section 16 to reach fluid absorption section 17. Otherwise, the positive and negative evaluations as well as the operations and advantages are similar to those of the second embodiment.

EXAMPLE 2

In example 2 the detectable material is the hepatitis B surface antigen HBsAg. Example 2 is performed according to the third embodiment as described above.

(1) Elements

Anti-HBsAg antibodies were bonded to 0.3 micron white latex, serving as particles 19. An anti-HBsAg antibody having a different epitope was bonded to colloidal gold, serving as the marking element. The bonding was performed using standard methods.

The reaction reagent was formed in the following manner. For the particles, 60 microliters was used per test at a concentration of 0.01%. This was mixed with 60 microliters of marking element per test at a concentration that provided absorbency of 0.6 for 520 nm light. This was applied to an intermediate section of a fiberglass pad, which served as the porous carrier. For the fluid application section, filter paper was connected to the glass pad. A nitrocellulose membrane (trade name SCHF from Millipoa Corp.) was used as the catching section. These were combined to form the detection apparatus.

(2) Tests and Results

Eighty microliters, each of a positive sample containing HBsAg and a negative sample not containing HBsAg, were absorbed into the fluid application sections. After fifteen minutes, the coloring at the catching sections were observed. For the sample containing HBsAg, coloring formed by the marking element appeared at the catching section in a range of 10 micrograms/ml–25 micrograms/ml. For the sample not containing HBsAg, no coloring was observed and a negative evaluation was made.

TABLE 1

|  | Desirable size | Example | More desirable size |
|---|---|---|---|
| Particles | 0.2–5 μm | 1 | approx. 1 μm white latex |
|  |  | 2 | approx 0.3–0.7 μm white latex |
| Marking elements | 0.02–0.6 μm | 1 | approx. 0.02 μm colloidal gold approx. 0.3 μm colored latex |
|  |  | 2 | approx. 0.02 μm colloidal gold |
| Porous carrier | 5–200 μm | 1 | approx. 100 μm fiberglass pad |
|  |  | 2 | approx. 100 μm fiberglass pad |
| Catcher | 0.3–20 μm | 1 | nitrocellulose membrane |
|  |  | 2 | nitrocellulose membrane |

Table 1 summarizes the materials used in Examples 1 and 2. In Example 1, according to the second embodiment of the present invention, the particle diameter is greater than the pore size, and the detectable material is hCG. In Example 2, according to the third embodiment of the present invention, the particle diameter is less than the pore size, and the detectable material is HBsAg.

According to the first technology of the present invention, an immunological complex is formed with the detectable material, after which a marking reaction is generated. Since detection is performed without using marking antibodies, precious antibodies need not be wasted. Furthermore, stearic hindrance and kinetic degradation due to the marking reaction is prevented, allowing the antigen-antibody reaction to proceed smoothly. Detection time is reduced and high sensitivity is provided.

Also, since marking is performed using immunological methods, markers such as water-soluble dies and the like can be used in addition to the conventional enzymes, colloidal gold, colored latex, and the like. This makes it possible to perform detection on materials that have been conventionally difficult to mark due to, for example, deactivation.

According to the second technology of the present invention, the concentration of the particles and marking elements is increased, the motion of the marking elements and particles is made more smooth, and detection sensitivity is increased. Also, the production process is simplified.

Having described preferred embodiments of the invention with reference to the accompanying drawings, it is to be understood that the invention is not limited to those precise embodiments, and that various changes and modifications may be effected therein by one skilled in the art without departing from the scope or spirit of the invention as defined in the appended claims.

What is claimed is:

1. An apparatus for detecting the presence of a detectable material in a sample comprising:

a fluid application section for contacting said sample;

a reaction reagent section, containing particles having antibodies which bind to the detectable material but which do not affect detection of said detectable material when not bound to said detectable material, and marking elements movably contained therein, said reaction reagent section connected to said fluid application section such that said sample moves from said fluid application section to said reaction reagent section; wherein said marking element comprises antibodies specific to the detectable material labeled with a detectable marker;

a porous carrier connected to said reaction reagent section such that said sample moves from said reaction reagent section to said porous carrier;

wherein a reaction product is formed from binding of said detectable material with both said marking elements and said particles when said detectable material is present in said sample; and a catching section in said porous carrier made from a material having a pore size smaller than a size of said reaction product, such that chromatographic movement of said marking elements not bonded in said reaction product is permitted through said catching section and chromatographic movement of said reaction product is restricted, because of the size of said reaction product, thereby causing said reaction product to be retained by said catching section.

2. The apparatus according to claim 1, wherein said pore size of said catching section is smaller than a the diameter of said particles.

3. The apparatus according to claim 2, wherein said detectable material is selected from at least one of human chorionic gonadotropin, luteinizing hormone, follicle stimulating hormone, thyroid stimulating hormone, insulin, and carcinoembryonic antigen.

4. The apparatus according to claim 1, wherein said pore size of said material of said catching section is larger than the diameter of said particles.

5. The apparatus according to claim 4, wherein said detectable material is selected from at least one of hepatitis B surface antigen, C-reactive protein, and hemoglobin.

6. A method for detecting the presence of a detectable material in a sample comprising:

contacting said sample with the apparatus of claim 1;

reacting the sample with said particles and with said marking elements such that said detectable material binds with both said marking elements and said particles when said detectable material is present in said sample to form a reaction product;

passing said sample, including any reaction product present, through said catching section; and analyzing the presence of said marking elements at said catching section, whereby the presence of said marking elements corresponds with the presence of said detectable material.

* * * * *